(12) United States Patent
Hadvary et al.

(10) Patent No.: US 10,478,550 B2
(45) Date of Patent: Nov. 19, 2019

(54) DEVICE WITH A LAVET-TYPE MOTOR

(71) Applicant: PharmaSens AG, Biel-Benken (CH)

(72) Inventors: Paul Hadvary, Biel-Benken (CH); Rudolf Dinger, Saint-Aubin (CH); Hansjorg Tschirky, Sissach (CH)

(73) Assignee: PHARMASENS AG, Biel-Benken (CH)

( * ) Notice: Subject to any disclaimer, the term of this patent is extended or adjusted under 35 U.S.C. 154(b) by 699 days.

(21) Appl. No.: 14/908,002

(22) PCT Filed: Aug. 26, 2014

(86) PCT No.: PCT/EP2014/068056
§ 371 (c)(1),
(2) Date: Jan. 27, 2016

(87) PCT Pub. No.: WO2015/028458
PCT Pub. Date: Mar. 5, 2015

(65) Prior Publication Data
US 2016/0166763 A1    Jun. 16, 2016

(30) Foreign Application Priority Data
Aug. 27, 2013  (EP) .................................. 13181870

(51) Int. Cl.
*A61M 5/142*  (2006.01)
*A61M 5/148*  (2006.01)
*A61M 5/172*  (2006.01)

(52) U.S. Cl.
CPC ...... *A61M 5/14216* (2013.01); *A61M 5/1483* (2013.01); *A61M 5/14232* (2013.01);
(Continued)

(58) Field of Classification Search
CPC .......... A61M 5/14216; A61M 5/14232; A61M 5/14248; A61M 5/1452; A61M 5/1483;
(Continued)

(56) References Cited

U.S. PATENT DOCUMENTS

| 4,138,617 A | 2/1979 | Sudler | |
| 4,544,329 A * | 10/1985 | O'Boyle | A61M 5/142 417/475 |

(Continued)

FOREIGN PATENT DOCUMENTS

| EP | 0388787 | 9/1990 |
| EP | 0447909 B1 | 7/1994 |

(Continued)

OTHER PUBLICATIONS

Definition of Lavet type steeping motor, Wikipedia free encyclopedia, https://en.wikipedia.org/wiki/Lavet-type_stepping_motor (Year: 1936).*

*Primary Examiner* — Manuel A Mendez
(74) *Attorney, Agent, or Firm* — Xsensus, LLP

(57) ABSTRACT

In a device for ambulatory wearing by the patient containing a pump for delivery of injection fluid or for removal of analysis fluid, the drive motor for the mechanically driven pump system is a Lavet-type stepper motor of small size designed for having a high mechanical power and low peak current requirement. Using this Lavet-type motor for syringe-type or peristaltic preferably patch-type pumps high infusion rates needed for e.g. bolus insulin injection or the delivery of therapeutic antibodies are achieved, and important safety features can be easily and reliably controlled, manufacturing costs get significantly reduced, and the overall size and weight of the device becomes smaller, for patient convenience.

26 Claims, 4 Drawing Sheets

(52) U.S. Cl.
CPC ...... *A61M 5/14248* (2013.01); *A61M 5/1723* (2013.01); *A61M 2005/14208* (2013.01); *A61M 2230/201* (2013.01)

(58) Field of Classification Search
CPC ............ A61M 5/1723; A61M 5/14228; A61M 2005/14208; A61M 2005/14252; A61M 2005/14268; A61M 2005/14506; A61M 2230/201; A61M 5/142; A61M 5/14244; A61M 5/16854; A61M 5/172; A61M 5/14212; A61M 5/16813; A61M 5/14276; A61M 5/14566; A61F 5/0053
See application file for complete search history.

(56) References Cited

U.S. PATENT DOCUMENTS

| | | | |
|---|---|---|---|
| 4,550,279 A * | 10/1985 | Klein | ........................ H02P 8/02 318/685 |
| 4,692,147 A | 9/1987 | Duggan | |
| 5,083,908 A | 1/1992 | Gagnebin et al. | |
| 2001/0016710 A1 | 8/2001 | Nason et al. | |
| 2007/0154336 A1 | 7/2007 | Miyazaki et al. | |

FOREIGN PATENT DOCUMENTS

| | | |
|---|---|---|
| EP | 0521184 B1 | 6/1995 |
| EP | 2438938 A1 | 4/2012 |
| FR | 823395 | 1/1938 |

\* cited by examiner

DEVICE WITH A LAVET-TYPE MOTOR

The present invention is related with devices for ambulatory use, having a mechanically driven pump with an electric motor.

One major field of application for this type of devices is the injection of physiologically active fluid into a patient. For this use the devices are usually equipped with an adhesive contact surface for attaching to a patient's skin or with a system for attaching to cloths and a cannula with or without a connecting tube for the access to the patient's tissue or vessels for introducing an injection fluid.

Injection devices are widely used in patient care but their size and complexity largely restricts their use to specialized facilities. Recently, ambulatory use of injection devices has been pioneered in diabetes care for the delivery of insulin. More recently, patch-type pumps are becoming the preferred option for patient convenience and safe use. These are devices which can be directly attached to the skin, having an infusion cannula incorporated and thus avoiding connective tubes to an infusion port.

Devices which can be attached directly to the skin are designed for a widespread use and not only have to meet the high functional and safety requirements but also have to be relatively small, light, robust, cost-effective and convenient for the patient.

Pumps driven by an electric motor are well established in such devices. For applications needing a high precision, like insulin delivery in diabetes patients injection devices typically use syringe-type pumps. In indications needing the delivery of higher volumes but allowing lower precision, e.g. for the delivery of therapeutic proteins, such as e.g. monoclonal antibodies, peristaltic pumps are a well established solution. Although alternative systems such as e.g piezo-system pumps are being developed, these systems have several draw-backs and syringe type or peristaltic pumps driven by an electric motor remain the best established and safe option.

The electric motors established as pump drives in such devices have several drawbacks. In particular, the generally used direct current (DC) or conventional stepper motors have intrinsic limitations in safety characteristics, manufacturing costs and battery size requirements. Although the overall electric power consumption is relatively small for all types of electric motors used, peak power requirements are different and have a direct effect on battery size and weight. Controlling potential safety hazards such as uncontrolled over-delivery or recognition of under-delivery due to the build-up of pressure in the delivery system necessitates additional components, complexity and costs.

In order to cope with the delivery requirements the electric motor of the pump system has to be powerful enough allowing a relatively high rate of injection, e.g. for bolus injections of insulin or the delivery of monoclonal antibodies. In addition, e.g. for insulin pump systems to deliver both, a rapid bolus injection and a slow basal infusion with high precision, a high dynamic range of several thousand of the motor drive is needed. In addition, the pump system has to be powerful enough to overcome a tissue back-pressure amounting sometimes to several bar and friction losses. In order to satisfy all these requirements the drive motor has to be able to deliver several mW of mechanical power.

Since this mechanical power needed can relatively easily be delivered by DC motors (be it brush-type or brushless motors) or by commercially available stepper motors, these motor types are generally used in such devices, e.g. in insulin pumps. The drawbacks, esp. for patch-type pump devices, of relatively large physical dimensions, too high peak currents for a small battery driven device and relatively high manufacturing costs are significant and it is desirable to find a better alternative. Moreover, the most important problem with these types of motors is that they are intrinsically not safe, needing a complex motor control system with several additional components and sensors to guarantee the high safety standards needed, and such a complexity has intrinsic hazards of failing, besides additional costs.

Lavet-type motors are well established in the watch and clock industry and have been described in EP0388787 as drives for a miniature peristaltic pump and in EP0447909 and EP0521184 the use of such a pump for the administration of therapeutic liquids, the advantage being mainly low manufacturing costs. On the other hand, the low mechanical power of the described motor used in the watch industry limits the use to indications needing very low delivery rates of about 0.1 mL per hour, which is by far too low for e.g. insulin bolus injections or the delivery rate needed for e.g. therapeutic antibodies. On the other hand, a significant increase of the mechanical power of Lavet-type motors, as would be needed for such indications is not obvious since e.g. the larger motors of clocks delivering a much higher torque have a much lower maximal rotor speed, and as a result the increase in mechanical power—being proportional to the product of torque and speed—in spite of the larger size, is small and by far not sufficient.

The key component determining the safety control measures needed and their complexity, as well as battery size, overall size and weight, and also the manufacturing costs is the motor driving the pump.

The aim of the present invention is to provide a drive motor for pump devices worn by the patient, esp. patch-type devices attached to the skin, which avoids the disadvantages of the state of the art pump motor drives and most importantly offers a high intrinsic safety and easy function control.

According to the invention this is achieved in that the motor used to drive the pump is a Lavet-type motor small enough for patch-type devices but having the necessary mechanical power and low peak current. In addition, intrinsic and design-controlled properties of this motor type together with analysis of the motor driving current pulse form are utilized for easy, and to a very high degree failure safe and low cost function-control of the device.

Lavet-type motors are well known in the wrist-watch and clock movement industry. They are robust and manufacturing is relatively easy and cost-effective. However they are not suitable for e.g. an insulin pump or for a pump for delivering the necessary high volumes needed for e.g. therapeutic antibodies since they do not deliver the needed mechanical power needed for this application.

Wrist-watch type Lavet motors, e.g. the one described in EP0388787 as drive for a miniature peristaltic pump have a torque which is typically below 0.3 µNm and even at their maximally possible speed of about 100 Hz the maximal mechanical power is far from the one needed for delivery rates in important therapeutic indications, e.g. for an insulin pump, or e.g. for the delivery of therapeutic proteins.

Indeed, as disclosed in EP0388787, a miniature peristaltic pump equipped with a watch type motor running at its speed limit is delivering only about 1.7 µL/min, whereas insulin pumps deliver for a bolus injection up to 120 µL/min, minimally 20 µL/min, and therapeutic proteins such as monoclonal antibodies are infused typically at more than 150 µL/min. Therefore, in the above mentioned patent in section [0022] it is explicitly stated that the disclosed solution for a sufficient miniaturization using a watch motor, is not useful for indications like e.g. diabetes, since it can deliver only at a very low rate which might be sufficient for the basal insulin infusion rate but far from being capable to deliver a bolus injection. In addition, for a basal infusion of insulin the intrinsic fluctuation of infusion rate with a peristaltic pump is problematic and therefore syringe-type pumps are preferred, needing a much higher power to move the piston even at very low infusion rates.

The larger Lavet-type motors used in the clock industry have a mechanical torque which is typically ten times higher than the Lavet-type motors of the wrist-watch industry, but due to their larger size, their maximum speed is 5 to 10 times lower. Therefore, the overall increase of mechanical power being proportional to the product of torque and speed is relatively small and not sufficient to generate the required mechanical power for pump motors for these indications, meaning that the required mechanical power can not be obtained with clock-type Lavet motors either.

One could of course further increase the size of Lavet-type motors used in the clock industry, but this could not solve the problem of torque and speed since larger motors inevitably became slower.

Increasing the size of a clock-type Lavet motor also means increasing its rotor dimensions, in particular its diameter. Larger rotor dimensions however lead to a larger moment of inertia of the rotor and thus to a slower motor. The moment of inertia I of a cylinder rotating around its axis is given by $$I=0.5 \cdot m \cdot r^2, \text{ or (dividing by } m\text{): } I/m=0.5 \cdot r^2,$$

where r is its radius and m its mass. The magnetic moment of the rotor which gives the torque of the motor is proportional to the rotor's volume, hence also proportional to its mass. The equation clearly shows, that, when the rotor size is increased (this means increasing its radius) the moment of inertia grows faster than the magnetic moment of the rotor which gives the motor's torque. Increasing the rotor size thus inevitably leads to slower motors, counteracting the gain in torque.

In addition, a larger motor requires more electric energy, in particular a higher operating current, thus also leading to the need for larger batteries, and overall inevitably leading to a significantly larger and heavier device.

Therefore, the use of Lavet-type motors known in the wrist-watch and clock movement industry is not obvious for pump drives requiring relatively high delivery rates such as indications like e.g. diabetes or the delivery of therapeutic proteins such as e.g. monoclonal antibodies since a simple "scale-up" would not lead to motors with the necessary mechanical power and it was doubtful if the necessary mechanical power can be met with Lavet-type motors of compact, small size and low peak current at all, enabling their application in the above mentioned important indications.

Surprisingly it was found, that this is possible by an optimized design resulting in a Lavet-type motor of compact size with the required mechanical power output. In addition, the high load torque and high rotation speed requirements can be combined with a low peak current of preferentially below 10 mA, which is typically 10 to 100 times lower than for conventional stepper motors used for such pumps. This relatively low peak current requirement of this Lavet motor which can be delivered by small button-type batteries, allows the desired further reduction in size and weight of the device, which is of prime importance especially for patch-type devices.

The Lavet-type motor according to the invention overcomes the mechanical power problem of the Lavet motors known from the watch and clock industry. Its dimensions, in particular the rotor diameter is similar to the one in the clock motor design, the rotor is however made of magnetic material having substantially better magnetic properties than the materials used in the clock industry.

It was found that with improved design and components of the Lavet-type motor, the efficient combination of these components, and importantly, by using the best known permanent magnet materials such as the Samarium-Cobalt alloys or Iron-Neodymium-Boron alloys and an optimized electrical drive scheme, not only motor torque could be increased by a factor of five to ten with respect to a clock-type Lavet motor, but also its maximal speed could be more than doubled. The mechanical power needed e.g. for a syringe-type insulin pump working in the bolus mode or the necessary delivery rate for e.g. therapeutic monoclonal antibodies using e.g. a peristaltic pump could thus be achieved with a Lavet-type motor of the size of a clock-type motor but with typically more than ten times higher mechanical power output.

In addition, it was found that important safety features, being critical for devices delivering therapeutic fluids, can easily and safely incorporated by making optimal use of intrinsic and design characteristics of the disclosed Lavet-type motor. This allows achieving a high level of operational safety for the device, without complex control systems, and therefore being considerably simpler, cheaper and more robust and less prone to failure as compared to state-of-the-art operation control systems needed with DC or conventional stepper motors.

The desired features guaranteeing a high safety level for pump operation include the fact, that proper design of the Lavet motor physically limits its operation to one rotation direction only and to a maximal torque and speed, with a holding torque higher than the load torque.

In addition, analysis of the motor driving current pulse form allows the control of the motor rotation speed in real time thus the recognition of a successful motor movement or motor stall and load torque determination for early recognition of delivery pressure build-up.

Further, the high holding torque of the Lavet-type motor allows using drive components with high efficiency, without the need for a complex unidirectional drive or a gear spindle with intrinsically low mechanical efficiency protecting against unintended backwards motion, to avoid the danger of back-flow following build-up of a high back-pressure.

In summary, according to the present invention a high level of operational safety can be achieved by making use of the advantages of the Lavet-type stepper motor over other stepper motors or DC motors. These include its intrinsic limits for unintended over-delivery, only unidirectional rotor movement, its easy control of the motor steps, and load torque determination eliminating the danger of under-delivery, its high holding torque allowing the use of a highly efficient drive. In addition, the relatively low peak current needed for operation allows the use of small batteries and the small and flat size, of the Lavet-type motor and gear drive are optimally suited for patch-type devices. Further advantages are low manufacturing costs and robust operation.

According to the invention, major problems with the motor drives of current, in particular patch-type injection devices are solved having the features disclosed herein below.

The subject injection device for introducing an injection fluid into a patient through the patient's skin or through an intravenous or intraperitoneal port comprises preferentially a syringe-type or a peristaltic pump actuated by a Lavet-type motor of small size designed for having a mechanical power high enough to enable delivery rates needed for many important indications like the delivery of insulin or of e.g. therapeutic proteins, like antibodies. Further, constructive and electronics features of the Lavet-type motor are designed and used to directly cover important safety features.

In addition, a device combining a reusable module with the motor, gear train, and its drive and control means with a disposable module containing the syringe or fluidics compartment of a peristaltic pump, the injection and the other components in direct contact with the patient's body solves sterilization requirements, is cost-effective and respects modern environmental requirements since it allows to reuse most of the pump's components multiple times. Furthermore this embodiment is also advantageous for filling with injection fluid. It allows filling of the syringe or fluidics compartment of a peristaltic pump before assembly of the two modules by simply injecting the fluid into the syringe or the fluidics compartment of a peristaltic pump e.g. through a septum by means of a needle.

In preferred embodiments the device has a contact surface for attachment directly to a patient's skin. Typically, the contact surface to the skin is coated with an adhesive and the pump is linked to a cannula having a tip which is configured and dimensioned for piercing the patient's skin or a septum of a port for introducing an injection fluid into the patient.

When used herein, the following definitions are used for the stated terms

Delivery of therapeutic liquid comprises both relatively fast injection (bolus) and relatively slow introduction (also called infusion or instillation) of a fluid into the body.

Drive and control means contains all necessary mechanical, electronics and software elements for the functionality of the device like, but not limited to, moving the piston of a syringe-type pump or the rotor of a peristaltic pump with the rollers compressing the flexible tube, according to internal or external signals, initiating, controlling and surveying the correct functioning of the device, interacting with external control devices, preferentially wirelessly, and giving warning signals if the device is not functioning properly.

Lavet-type motor is the simplest type of a stepping motor following the principles described by the French engineer Marius Lavet (FR 823395 patented in 1938) and further developed by the watch industry (see for instance U.S. Pat. No. 4,550,279 by Eric Klein). It is typically used as reliable, low-cost but low-torque driving motor in watches and clocks. The Lavet-type motor has only one coil, a stator, and usually a cylindrical rotor with a permanent magnet. The axis of rotation is usually along the axis of the cylinder and magnetization is in the direction of the cylinder diameter. The magnetic flux of the rotor creates a flux in the stator magnetic circuit which strongly varies with the angular position of the rotor. This leads to the situation that the magnetic flux in the stator passes from positive to negative values when the rotor turns a full turn and generally behaves similar to a cosine function. The variation in the magnetic flux causes a torque in the rotor even if there is no current in the coil, causing the rotor to take two stable positions. These two angular positions are the stable rest positions of the rotor and the rotor takes these two positions even if there is no current applied to the coil. The rotor thus takes one of these stable positions and stays there without the need to power the motor.

In order to have the rotor turn by one step, which means by 180° an electric pulse is applied to the motor coil. The electric pulse creates a current in the coil and thus a magnetic field and a magnetic flux in the stator. If the polarity of the electric pulse is such, that the created magnetic flux corresponds in its polarity to the flux created by the rotor, no torque is created at the rotor and it stays in its rest position. If however the electric pulse is of opposite polarity, the magnetic flux created by the coil also changes its sign and creates a torque in the rotor turning it by 180°. This simple behaviour of the motor allows a correspondingly simple motor control by applying alternatively a positive and a negative voltage pulse to the coil.

Patch-type devices can be directly attached to the skin with an adhesive layer and have an infusion cannula incorporated. Such an application imposes severe limitations in size, form and weight for safe and convenient wearing. Besides a convenient, preferably round or slightly oval shape not exceeding 6 cm in diameter, a limited overall height, preferably below 1.7 cm, and an overall weight below 50 g should be achieved. Thus, motors and drives allowing a flat design and working with small, button batteries have a strong advantage for such devices. The Lavet-type motor drive according to the subject invention is the ideal motor for a device meeting these requirements.

Peristaltic pump has a reservoir connected to an elastic tube and a rotor with a number of rollers or fingers, attached to the external circumference of the rotor compressing the flexible tube fitted inside a pump casing. As the rotor turns the part of tube under compression by the roller or finger gets occluded thus forcing the fluid within the tube to move through the tube. As the tube opens to its natural state after the passing of the cam, fluid flow from the reservoir is induced to the tube. Preferentially, there are two or more rollers or several fingers occluding the tube, trapping between them a portion of fluid which is then transported toward the pump outlet connected to the infusion cannula.

Peristaltic pumps have the advantage that the reservoir has not to be pressurized, as compared e.g. to syringe type pumps and they can deliver with rapid flow rate against a high back-pressure with minimal force, since the diameter of the tube is relatively small. On the other hand, precision is intrinsically much lower than e.g. of syringe type pumps and fluid flow pulsates.

Syringe-type pump has a cylindrical reservoir with a constant, preferably circular cross section as barrel. A piston tightly fitting in the interior of the barrel is passed along the barrel by means of a piston-rod actuated by drive means and an electric motor. The syringe can be straight or circular, as described e.g. in WO 2012/049080. The motor is usually a DC motor or a stepping motor. According to the subject invention the syringe-type pump is driven by a Lavet-type motor offering several advantages.

In the following preferred embodiments of the invention are exemplified, with reference to the accompanying drawings in which FIG. 1 is a diagrammatic view of an injection device with a circular syringe pump and a drive mechanism for the piston rod comprising a gear train and a Lavet-type motor according to one embodiment of the invention.

Figure 1A:
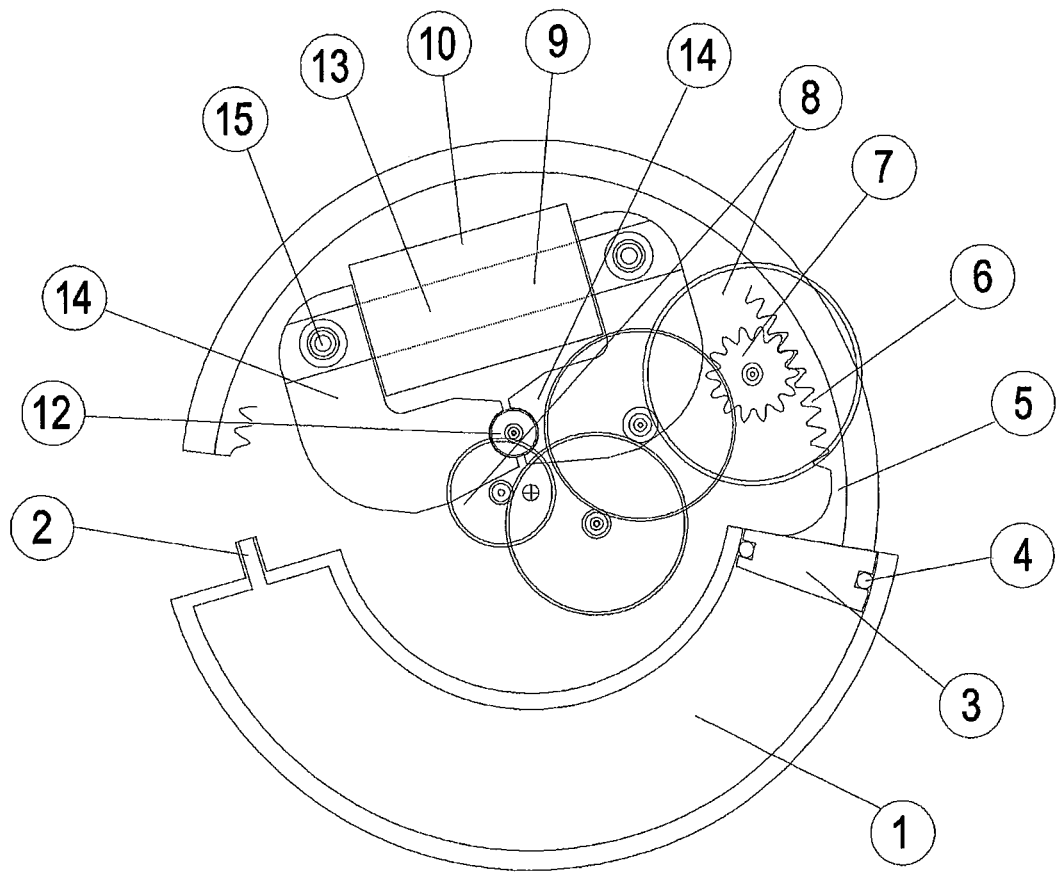

FIG. 1A shows an injection device as a sectional top view. In this embodiment of the invention a syringe-type e.g. insulin pump has a barrel in form of a segment of a toroidal tube 1. One end 2 of the barrel is provided with a connecting channel to a cannula (not shown).

A piston 3 is arranged in the interior of the barrel and is provided with a seal 4 fitting tightly the inner wall of the toroidal barrel. The piston is connected to a driving rod 5 which is circularly shaped for driving the piston through the entire length of the barrel.

The inner side of the driving rod 5 has a gear rim 6 which is driven by a gear drive 7. The gear drive is driven e.g. by a gear train 8 and a Lavet-type motor 9 which can be regulated for controlled delivery by signals from inbuilt and/or remote control elements (not shown in the figure). The Lavet-type motor consists of a coil 10, a stator 11 and a rotor 12. In this embodiment the stator consists of 3 parts: a ferromagnetic core 13 within the coil and two pole pieces 14 embracing the rotor and being magnetically connected to the core by means of screws 15 pressing the core and the pole pieces together.

A Lavet-type motor has only one coil and a rotor with one diagonally oriented magnetization. If the motor design would be symmetrical, the rotor would go in a rest position where the rotor magnetization also satisfies the symmetry, this means where it is parallel to the coil axis. There are obviously two such positions differing by a 180° rotation of the rotor. If in a perfectly symmetrical design a current pulse is applied to rotate the rotor by 180°, the rotor can do this movement by rotating clockwise or counter clockwise, there is no preference for either rotation direction.

In order to achieve a defined direction of rotor movement, the stator is designed asymmetrically causing the rotor to take rest positions where the magnetization direction has an offset angle with respect to the symmetrical position. Applying such a stator design the motor will always turn in the direction allowing the rotor to turn its magnetic dipole axis with the smallest rotation angle parallel to the magnetic field produced by the stator. For these reasons the rotation direction is given by the rest position of the rotor which is in turn given by the mechanical design of the stator. Of importance, by closing the magnetic flux of the rotor through the stator, the rotor is kept in either of the two rest positions rotated by 180°, adapted without the need to create a magnetic field in the coil of the motor, and thus without the need to power the motor to keep the rotor in a stable position.

Figure 1B:
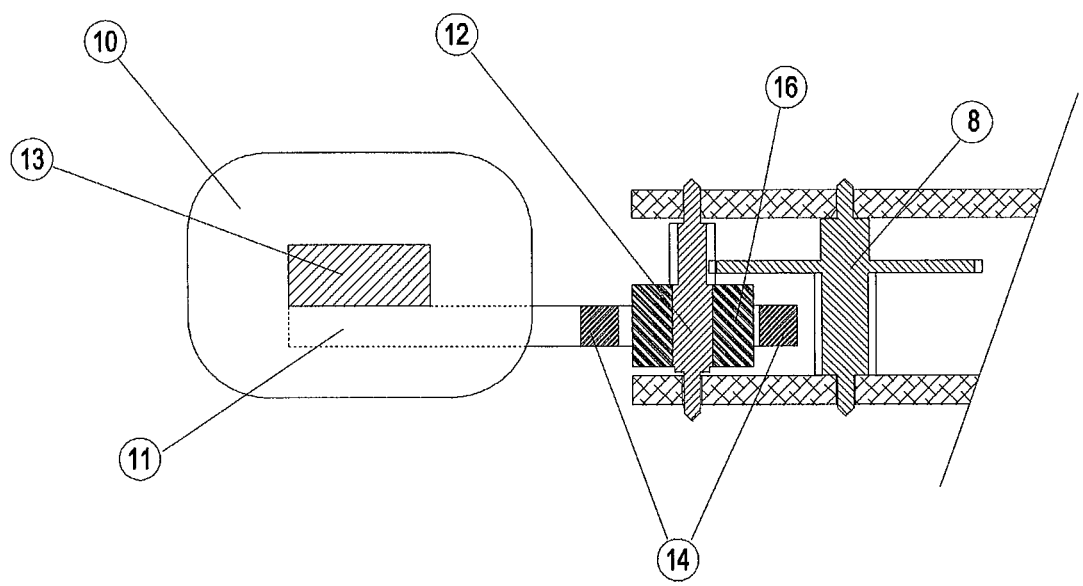

In FIG. 1B the Lavet-type motor is shown in a cross-section perpendicular to the axis of the coil 10. The cylindrical rotor 12 with a permanent magnet 16 has its axis of rotation along the axis of the cylinder and magnetization is in the direction of the rotor cylinder diameter.

Optimization of the motor design by carefully balancing coil turns and resistance with stator geometry and the use of high efficiency magnetic materials for the rotor magnet allows to reach the necessary mechanical power output for driving the pump and to sufficiently reduce the peak current drawn from the battery.

In order to reach the required torque and speed requirements resulting in typically more than ten times higher mechanical power as compared to a clock-type motor of similar size the rotor magnet is made of a magnetic material with high energy density, e.g. an alloy including rare earth magnetic elements, such as Samarium-Cobalt (SmCo) or preferentially Iron-Neodymium-Boron (FeNdB). Optimization of all these design features allows designing a small and compact Lavet-type motor with sufficient load torque, high rotor velocity and an overall efficiency of over 30%, having a small peak current requirement at 1.5 or 3 Volts which can be directly drawn from small watch type button cells.

In a typical example a Lavet-type motor as schematically depicted in FIGS. 1A and 1B having the required torque and speed requirements has a rotor 12 with a bipolar rotor magnet 16 of FeNdB with a height of 2 mm and an outer diameter of 3 mm on a shaft integrating the pinion driving the gear train. The ferromagnetic circuit has a stator 11 with two pole pieces 14, each of them being pressed against the coil core 13 by means of screws 15 or similar assembly techniques. The stator has a height of 1.6 mm, with a central stator hole of 3.5 mm diameter for embodying the rotor 12 and a linear shifting between the stator poles of 0.125 mm. Its form is optimized for smallest foot-print but large enough to avoid saturation of the magnet flux. The coil core 13 has a width of 3.5 mm and a height of 1.6 mm. For the coil core and the stator a Nickel-Iron alloy with 50% Nickel content was chosen.

The driving coil 10 wound directly on the coil core 13 has a length of 14.2 mm, a resistance of 150Ω and contains 3,000 turns. Supplied with a bipolar pulse of 20 ms using a 3V battery (dropping in the worst case to 2.4 V during life-time), the rotor delivers a load torque of 45 µNm and can be run with up to 30 steps per second, covering 180° per step. At full load the motor consumption is 175 µAs per pulse, with a peak current of 10 mAmp allowing the use of small button-type batteries. The peak current can even be further reduced using chopped pulse techniques.

This Lavet-type motor allows the design of a small size pump combining the requirements of rapid dosing e.g. for insulin bolus injections or application of e.g. therapeutic proteins such as therapeutic antibodies, high resolution for e.g. low basal insulin infusion rates and enough injection pressure capabilities to overcome significant back-pressure sometimes encountered during infusion.

Figure 2:
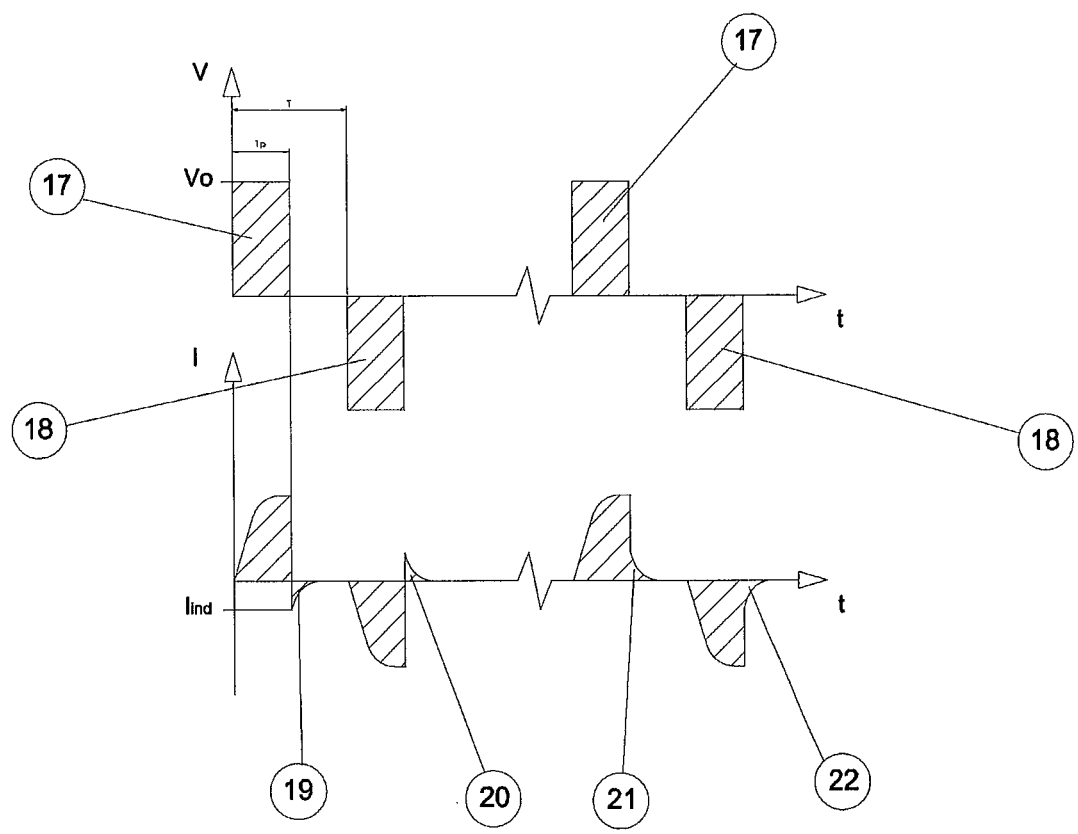
FIG. 2 is a schematic presentation of the current characteristics for a Lavet-type motor designed for the infusion of therapeutic liquids.

FIG. 2 shows the typical voltage (upper figure) and current signals (lower figure) of such a Lavet-type motor. The motor control unit generates pulses 17 and 18 alternatively of opposite polarity for a period of $T_p$, which is shorter than the period T needed for the rotor to perform the step of 180°. This pulse can be generated e.g. with a voltage directly provided by the battery of 1.5 or 3 Volts.

The left part of the figure illustrates the situation in case of two successful half-turns of the rotor. The pulses 17 and 18 applied to the coil result in a magnetic flow by which the rotor is rotated out of its rest position and accelerated until it makes a turn of at least 90°. After switching off the voltage pulse the rotor continues to turn because of its inertia and is pulled into the next rest position by the zero current torque, thus completing the 180° step.

With devices for the administration of therapeutic fluids reliable safety systems to guarantee correct functioning is of prime importance. For example safety features of insulin pumps must exclude unintended under-delivery or, even more importantly over-delivery of insulin in case of an electronics failure.

Some unique features physically determined by proper design of such a Lavet-type motor offer the possibility to directly cover important features ensuring safe functioning being significant advantages in providing easy, robust and cheap means to satisfy these safety requirements, such as only-unidirectional rotor movement, need for alternatively positive and negative current pulses for movement, design-limited maximal torque and maximal speed and a high electric powerless holding torque.

In addition, analysis of the form of the motor driving current allows safe recognition of a successful motor movement or motor stall, and load torque determination for early recognition of delivery pressure build-up.

The optimized mechanical design, mainly the shape of the stator, of such a Lavet-type motor ensures that it can only turn in one direction:
- If the current pulse is of the wrong polarity (with respect to the rest position of the rotor) the rotor will show a small oscillation movement and fall back into its rest position when the pulse stops.
- If the current pulse is of correct polarity but too short or too small, the energy supplied to the motor is insufficient to do the motor step. In such a situation the rotor will move in the correct direction, but fall back into its original rest position.
- If the current pulse is of correct polarity and duration the rotor will do its step correctly and fall into the rest position at 180°.
- If the pulse is of correct polarity and too long the rotor will correctly turn and do its step but it will be held in a position which is slightly over the rest position at 180° for as long as the pulse lasts and fall back in its correct rest position when the pulse stops. In this case the motor does its correct step; it however needs as long for this step as the current pulse lasts.

Thus, even with erroneous electric drive pulses a Lavet motor can only do the correct step or stop. A backwards movement is not possible with this motor design.

The high detent torque/holding torque of this Lavet-type motor, being about 1.5 times higher than the maximal load torque, secures that the motor has a sufficient breaking effect at standstill allowing the use of a highly efficient drive having only toothed gears without any additional means to protect against unintended backwards movement. In state-of-the-art e.g. insulin syringe pump devices using DC or stepper motors the gear-drive has to include also a self-locking element, e.g. a spindle with a high friction, massively decreasing the overall efficiency of the drive. Alternatively, a separate break is needed, e.g. on the motor axis, which constitutes an additional element, is consuming additional electrical energy and further decreases overall efficiency.

As a result, with the high efficiency of the optimized Lavet-type motor combined with an optimized normal gear-drive, an overall efficiency of about 20% can be achieved. Further, a relatively low peak current requirement allows the use of small watch type button cells for the device, in contrast to at least AAA batteries normally required for such pumps, an important advantage for a patch-type device directly adhering to the skin.

As shown in the lower part of FIG. 2 the relatively fast turning rotor acts as a generator and induces a significant current $I_{ind}$ 19 and 20, respectively in the motor coil when the external voltage is turned off. If the motor successfully performed its step, the induced current is of opposite polarity with respect to the applied voltage pulses 17 and 18. The right part of the lower figure illustrates the situation in case of a non-successful rotor step. After the voltage pulse 17 or 18, the rotor falls back to its starting rest position and the generator current $I_{ind}$ 21 or 22, respectively is of the same polarity as the applied pulse.

This allows a safe and easy direct control of rotor steps, without the need for additional complex sensor systems. For the detection if a rotor step has been made successfully or unsuccessfully, the current signal can be easily measured: opposite polarity compared to the applied pulse meaning successful step and same polarity meaning non-successful step.

Further, the magnetic stray field changes its polarity with each rotor step of 180° allowing an easy second and independent control of rotor steps with a simple sensor placed close to the rotor, such as e.g. a Hall sensor, detecting the magnetic stray field of the rotor permanent magnet. Both of these methods to control the rotor movement are easy and cheap to realize and result in a very high degree of safety, being of prime importance for e.g. insulin pumps.

An additional advantage results from control of the necessary pulse period $T_p$, which is dependent on the necessary torque for a step, allowing early detection of increasing pressure for delivery of the therapeutic liquid.

The maximum speed of stepper motors is restricted by the design and its physical working principle, thus limiting the danger of e.g. unintended insulin over-delivery in case of failures in the electronics—in case of electronic failures a stepping motor, contrary to DC motors, normally stops. The Lavet-type motor is even safer than normal stepper motors, since the drive scheme requires for consecutive steps the change in polarity of the applied pulse and no complicated phase scheme driving different coils has to be applied. This is an important safety factor in case of failures in the electronic motor drive control.

Further, the detection of a successful step from the motor signals as described in FIG. 2 is much easier and more reliable than with conventional stepper motors. In addition, separate sensors for detection of a successful step of the rotor are for Lavet-type motors, such as e.g. Hall sensors, smaller and much cheaper than rotary encoders needed for the detection of a successful step of a conventional stepper motor.

Although the Lavet-type motor disclosed here as superior drive motor for syringe type or peristaltic pumps represents a stepper motor in its simplest form, its advantages for these applications are significant not only compared to DC motors but also compared to conventional stepper motors and especially important for safety aspects and overall device costs.

In addition, in devices with a peristaltic pump the easy regulation of Lavet-type motor step frequency allows to attenuate the flow pulsation intrinsic to this type of pumps and representing a significant dosing problem especially at low infusion rates, e.g. for basal-rate insulin delivery. Adapting the motor step frequency to the angular position of the rollers' position occluding the peristaltic delivery tube allows approaching a constant flow rate much more efficiently than e.g. by using the constructively complicated and therefore less safe solution of two connected peristaltic tubes pumping in parallel, with their rollers displaced by half the angle between consecutive rollers of the other channel, as disclosed e.g. in EP0388787. Having two connected peristaltic tubes working in parallel has the additional disadvantage being prone to capture air bubbles in the connecting pieces which are problematic for infusion devices.

Peristaltic pumps e.g. for the delivery of therapeutic proteins at a relatively high infusion rate are preferentially driven by a Lavet-type motor as disclosed in the present invention, but it is advantageous to keep the peak mechanical power needed as low as possible. This can be done by an optimized construction of the pump head. A large portion of the mechanical power needed with peristaltic pumps comes from compression of the elastic peristaltic tube by the rollers pressing it against the pump casing. An almost equal mechanical power is delivered by the decompression of the elastic tube when the tube opens to its natural state during passing of the roller, and therefore the decompression torque compensates the compression torque during entering of the roller the compression segment. In a design optimized for low mechanical power needs, this effect of torque compensation for tube compression by torque gain during tube opening can be achieved if simultaneously to a roller entering the compression section an other roller is leaving the compression section. Therefore, for minimizing the mechanical power needed, the rollers and the form of the tube support of the pump casing against which the peristaltic tube is pressed by the rollers should be designed and constructed such, that occlusion of the tube by the roller rolling-on, and opening of the tube to its natural state during the passing of the roller rolling-off, respectively takes place synchronously.

Figure 3:
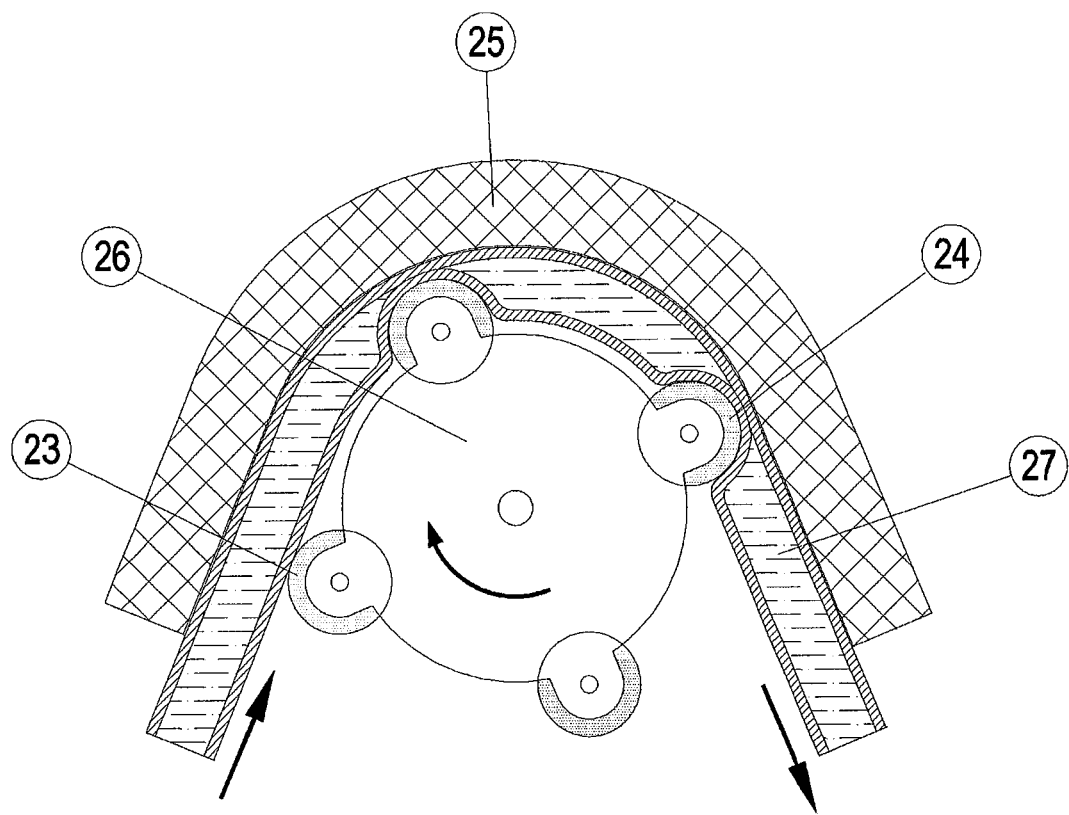
FIG. 3 is a schematic presentation of the pump head of a peristaltic pump according to one embodiment of the invention.

FIG. 3 shows schematically such an arrangement of a peristaltic pump head resulting in occlusion of the tube by the roller rolling-on, and opening of the tube to its natural state during the passing of the roller rolling-off, respectively, taking place synchronously. This can be achieved e.g. by having four compression rollers 23 and 24 attached to the external circumference of the rotor 26 moving the compression rollers around its wheel. The tube support 25 of the casing determines the compressing section for the flexible peristaltic tube 27 fitted inside the pump casing and forming a 135° segment of a circle with tangential inlet and outlet of the tube. The 135° angle is specific for the design with 4 rollers of the example chosen in FIG. 3; this angle obviously varies with different designs, particularly if the number of rollers is modified. The figure shows the principle of compensation of the torque needed for the entering roller 23 by the leaving roller 24. The position depicted in the figure shows the leaving roller 24 being just at the end of the circular compressing section of the tube support 25 and the entering roller 23 just starting touching the tube.

Further advantages of a Lavet-type motor as compared to a conventional stepper motor are the intrinsically compact and flat design and the low peak current requirement being about a factor 10 to 100 lower than with conventional stepper motors, thus allowing operation from small button batteries. Both of these advantages are especially important for patch-type devices, allowing reducing size and weight, which are important aspects for patient convenience.

With DC motors, the maximum speed increases with the supply voltage and can in an application such as e.g. the insulin pump become dangerously high. In contrast to stepper motors which are regulated at constant voltage by the frequency of the applied current pulses, DC motors are regulated by the driving voltage. The dosing rate of e.g. an insulin pump varies over a wide range; they are typically specified to cover a dosing rate range of several thousand.

Since DC motors are controlled by varying their supply voltage it is obvious that such a wide range of motor speed can only be achieved with closed loop regulation systems using the feed-back of a rotation sensor on the motor shaft. In case of a failure in the regulating electronics or even more in case of a short circuit, very high turn rates with dangerous over-delivery can result. The situation with a DC motor is aggravated by the torque characteristics of DC motors. If the load increases, a DC motor will increase the current drawn from the supply and strongly increase the torque. The motor will therefore force the pump even if the (too) high dosing rate creates an important back-pressure. In order to ensure that this does not result in undetected leakage problems of the delivery system, additional measures such as e.g. pressure sensors have to be added for the control of the maximally allowable pressure.

The torque of stepper motors, including the Lavet-type motors, is intrinsically limited by their very principle, and therefore they are unable to deliver a higher torque than what they have been designed for. Therefore, DC motors are intrinsically less safe for pumps delivering therapeutic liquids and need complex and expensive control mechanisms.

The Lavet-type motor has an additional advantage in that the rotor is held firmly in both rest positions after each step due to closure of the rotor's magnetic flux by the stator. In contrast to both, conventional stepper motors and DC motors, the Lavet-type motor has a significant holding torque without application of electrical power, and the optimized Lavet-type motor design for delivery of therapeutic liquids disclosed in this invention allows obtaining a withholding torque which is higher than the load torque, obviating any potential danger of back-flow from overpressure.

This is an additional significant advantage especially for syringe-type pumps, since as mentioned, there are delivery conditions where the body tissue creates a significant back pressure having the tendency to move the pump backwards. This must be avoided in any case. Pump drives using normal stepper or DC motors are normally equipped with gear drives having mechanical means to ensure unidirectional operation of the movement (this means are blocking the movement if a reverse movement e.g. of the syringe piston tries to drive the motor backwards). Unidirectional gear trains e.g. screw drives, have however inherent disadvantages in terms of mechanic efficiency, or have reliability problems as in the case of unidirectional toothed wheel gears.

In summary, a Lavet-type motor is much safer and control of successful steps is much easier than with the state-of-the-art DC or stepper motors.

In preferred embodiments of the invention the device is composed of two parts, a reusable part comprising the motor, the gear train, and the control elements and a disposable part comprising other elements, especially the ones which should be used only once, like the reservoir and the parts of the pump system which are in direct contact with the injection liquid. In case of a patch-type pump directly adhering to the skin also the cannula for delivering the injection fluid and the adhesive for attachment to the skin should be part of the disposable part.

With peristaltic pumps the drive means of the reusable part contain preferentially in addition to the motor, gear train, and the control elements also the rollers attached to the external circumference of the rotor and compressing the flexible tube, whereas the peristaltic tube connected to the reservoir is part of the disposable part. With e.g. the pump head shown in FIG. 3 coupling is straight-forward by a mechanism ensuring the necessary pressure on the peristaltic tube between the rollers and the tube support of the pump body. Preferentially, as part of this coupling process and before tightening the peristaltic tube by the pressure of the rollers, enough fluid from the reservoir is pressed out to completely remove any air from the peristaltic tube.

For syringe-type pumps the drive means of the reusable part couple to the fluid moving means of the disposable part preferentially by means of a self-adjusting gear-gear connection. In one embodiment of the subject invention the self-adjusting gear-gear connection is an axially sliding gear of the gear train engaging with the gear of the toothed piston moving rod of the syringe.

Filling the reservoir with injection fluid before assembly of the reusable and disposable parts does not require a rewind by the drive, introducing additional problems of speed requirements and the need for two-directional movement requiring stringent and relatively complex control of the movement direction, e.g. by a two-channel shaft encoder.

Filling of the reservoir of the disposable part before engagement with the motor and drive gear-train is an easy, fast and safe process, since it can be done e.g. with a syringe under positive pressure, also reducing the danger for introducing air bubbles. In addition, full advantage can be taken from using the Lavet-type motor with a high holding torque allowing a unidirectional highly efficient drive having only toothed wheel gears.

Upon reading this specification, various alternative embodiments will become obvious to the skilled artisan. For example, the syringe of a syringe-type pump can have a straight barrel and driving rod and also alternative mechanical injection fluid reservoir emptying means, such as e.g. flexible bags with a mechanical pressing mechanism could be advantageously driven by a Lavet-type motor.

The major advantages of the device driven by a Lavet-type motor described above are the ease to ensure superior safety and control of operation and the simple constructive structure consisting of only few parts. Further, many complex and costly control elements for safe function are either already intrinsically given by the construction of the Lavet-type motor or are much easier to realize. In addition, both the motor and the safety elements can be manufactured significantly more cost-effectively than if conventional stepper or DC motors are used. Further, the disclosed Lavet-type motor having a high load torque and high rotation speed simultaneously resulting in the needed mechanical power is relatively flat, has low peak energy requirements, and with a drive having only toothed gears, the overall efficiency is high, allow using smaller batteries. These features have in addition to cost-effectiveness and superior safety a significant impact on overall size and weight, thus increasing patient convenience.

The invention claimed is:

1. A device for ambulatory wearing by a patient, comprising:
    a pump for delivery of injection fluid including a pump system with a fluid reservoirs; and
    a Lavet-type stepper motor to drive the pump system, the stepper motor including a rotor with a magnet made of high energy density magnetic material which is a magnetic alloy including a rare earth element,
    wherein when the stepper motor successfully performs a step, there is an induced current of opposite polarity with respect to applied voltage pulse, and when the stepper motor does not successfully perform the step, there is an induced current that is of a same polarity with respect to the applied voltage pulse,
    wherein a maximum speed of the stepper motor is restricted by a design of the stepper motor,
    wherein a maximum torque of the stepper motor is restricted by a design of the stepper motor,
    wherein the injection fluid includes therapeutic proteins like insulin or antibodies.

2. The device according to claim 1 wherein constructive and electronics features of the Lavet-type motor are designed and used to:
    provide high powerless holding torque, and
    allow detection of necessary torque for the step.

3. The device according to claim 1 wherein the rotor magnet is made from a Samarium Cobalt (SmCo) alloy or from an Iron Neodym Boron (FeNdB) alloy.

4. The device according to claim 1 wherein the pump system includes a syringe having as reservoir, a tubular barrel with a connecting opening in a vicinity of one end of the barrel for the passage of fluid, and a piston movable along an axis and fitting in the interior of the barrel with a piston moving rod for moving the piston.

5. The device according to claim 4 wherein the barrel has a toroidal shape, and the piston moving rod is circularly bent curved and corresponds to the axis of the barrel.

6. The device according to claim 1 wherein the pump system includes a flexible bag reservoir and a plunger squeezing the bag.

7. The device according to claim 1 wherein the pump system includes a peristaltic pump with a reservoir.

8. The device according to claim 7 wherein pulsations in delivery are minimized by regulating the motor step frequency.

9. The device according to claim 7 wherein rollers compressing a peristaltic tube and a form of the pump casing against which the peristaltic tube is pressed by the rollers are arranged such that occlusion of the tube by the roller rolling-on and opening of the tube to its natural state after the passing of the roller rolling-off, respectively takes place synchronously and thus largely eliminates the motor torque needed for compression of the tube by the roller rolling-on.

10. The device according to claim 1 further comprising a motor control system comprising a drive electronics component, an operation control component and a control unit for programming pump function.

11. The device according to claim 10 wherein the operation control component has an element for adjusting a motor pulse duration and/or a pulse voltage in order to determine a torque the motor is delivering to the pump.

12. The device according to 10 wherein the operation control component has an element analyzing motor current and/or voltage to control the motor steps.

13. The device according to claim 10 wherein the operation control element has a magnetic field sensor to control the motor steps.

14. The device according to claim 10 wherein the operation control element is controlling over-delivery or under-delivery and other safety related features and alarms.

15. The device according to claim 1 wherein a control unit for programming pump function has a remote element connected by a wireless link.

16. The device according to claim 15 further comprises an inbuilt or remote diagnostic probe, generating signals for the control unit.

17. The device according to claim 16 wherein the diagnostic probe is a glucose sensor generating signals for controlling insulin delivery.

18. The device according to claim 1 wherein the device is an insulin pump.

19. The device according to claim 1 wherein the pump is collecting body fluid samples for analyte determination.

20. The device according to claim 1 further comprising an adhesive contact surface for contacting the patient's skin and adhering the device to the patient's skin.

21. The device according to claim 1, wherein the device includes a reusable part comprising the stepper motor and control elements, and a disposable part comprising other elements.

22. The device according to claim 21, further comprising:
    a self-adjusting gear-gear connection coupling the stepper motor and the pump system.

23. The device according to claim 21 wherein the reservoir is filled before assembly of the reusable and disposable parts, before coupling of the stepper motor and the pump system, and not requiring a rewind by the stepper motor.

24. The device according to claim 1 further comprising:
a cannula having a tip for piercing the patient's skin; and
a diagnostic probe.

25. The device according to claim 1 further comprising:
an adhesive layer fixed on the device for adhering to skin of the patient.

26. The device according to claim 1 wherein the device is applied to the skin using a functional package with a pressing an adhesive layer towards the skin and protecting release and actuation elements of the device against unintended activation.

\* \* \* \* \*